(12) United States Patent
Jo et al.

(10) Patent No.: US 10,807,923 B2
(45) Date of Patent: Oct. 20, 2020

(54) METHOD FOR DEHYDROGENATING ALKANE

(71) Applicant: HYOSUNG CHEMICAL CORPORATION, Seoul (KR)

(72) Inventors: Bu Young Jo, Anyang-si (KR); Won Il Kim, Seongnam-si (KR)

(73) Assignee: HYOSUNG CHEMICAL CORPORATION, Seoul (KR)

( * ) Notice: Subject to any disclaimer, the term of this patent is extended or adjusted under 35 U.S.C. 154(b) by 0 days.

(21) Appl. No.: 16/477,068

(22) PCT Filed: Jun. 29, 2017

(86) PCT No.: PCT/KR2017/006867
§ 371 (c)(1),
(2) Date: Jul. 10, 2019

(87) PCT Pub. No.: WO2018/135712
PCT Pub. Date: Jul. 26, 2018

(65) Prior Publication Data
US 2019/0352240 A1    Nov. 21, 2019

(30) Foreign Application Priority Data

Jan. 18, 2017   (KR) .................... 10-2017-0008656

(51) Int. Cl.
*C07C 5/333* (2006.01)
*C07C 5/32* (2006.01)
(Continued)

(52) U.S. Cl.
CPC .............. *C07C 5/333* (2013.01); *B01D 53/04* (2013.01); *B01J 19/0013* (2013.01);
(Continued)

(58) Field of Classification Search
CPC .. C07C 5/333; C07C 7/00; C07C 7/12; C07C 7/005; C01B 3/56; B01D 53/04
See application file for complete search history.

(56) References Cited

U.S. PATENT DOCUMENTS 2,621,216 A * 12/1952 White .................... C07C 11/04
585/636
3,437,703 A *  4/1969 Mayfield ................ C07C 5/48
585/443
(Continued)

FOREIGN PATENT DOCUMENTS

KR    10-2011-0008035 A    1/2011
KR    10-2015-0062934 A    6/2015
(Continued)

OTHER PUBLICATIONS

International Search Report and Written Opinion issued for PCT/KR2017/006867, dated Oct. 18, 2017, with English translation of International Search Report, 11 pages.

*Primary Examiner* — Youngsul Jeong
(74) *Attorney, Agent, or Firm* — Hamre, Schumann, Mueller & Larson, P.C.

(57) ABSTRACT

The present invention relates to a method for dehydrogenating an alkane, the method including: a step of feeding into dehydrogenation reactors a feed gas stream containing a hydrocarbon to be dehydrogenated, hydrogen, and steam and performing dehydrogenation, wherein the dehydrogenation step is repeated in five or more sets, the dehydrogenation reactors have two parallel-connected reaction material heaters configured to heat the feed gas stream which is fed into each of the dehydrogenation reactors, and the steam is fed separately to the individual reactors for five or more sets of dehydrogenation steps; and a step of cooling and compressing a production gas stream resulting from the previous step, quenching the compressed product gas stream (Continued)

by passage through a cooling box, separating and purifying the product gas stream having passed through the cooling box, and recovering a product.

8 Claims, 2 Drawing Sheets

(51) Int. Cl.
- *B01J 19/00* (2006.01)
- *B01D 53/04* (2006.01)
- *B01J 19/24* (2006.01)
- *C01B 3/56* (2006.01)
- *C07C 7/00* (2006.01)
- *C07C 7/12* (2006.01)

(52) U.S. Cl.
CPC ............... *B01J 19/245* (2013.01); *C01B 3/56* (2013.01); *C07C 7/005* (2013.01); *C07C 7/12* (2013.01); *B01D 2253/1124* (2013.01); *B01D 2257/502* (2013.01); *B01J 2219/00103* (2013.01); *B01J 2219/00117* (2013.01); *C01B 2203/042* (2013.01); *C01B 2203/047* (2013.01)

(56) References Cited

U.S. PATENT DOCUMENTS

| | | | |
|---|---|---|---|
| 4,376,225 A | * | 3/1983 | Vora .................. C07C 5/333 585/658 |
| 6,472,577 B1 | | 10/2002 | Zimmermann et al. |
| 2009/0264692 A1 | * | 10/2009 | Welch .................. C07C 5/3332 585/440 |

FOREIGN PATENT DOCUMENTS

| | | |
|---|---|---|
| KR | 10-2016-0022313 A | 2/2016 |
| KR | 10-2016-0047066 A | 5/2016 |
| KR | 10-2016-0071114 A | 6/2016 |

\* cited by examiner

METHOD FOR DEHYDROGENATING ALKANE

TECHNICAL FIELD

The present invention relates to a method for dehydrogenating an alkane, and more specifically to a method for dehydrogenating propane to produce propylene.

BACKGROUND ART

In the petrochemical industry, continuous catalytic conversion is carried out. A moving catalyst dehydrogenation process for hydrocarbons is an important process in the production of light hydrocarbon components, and is an important process in the production of ethylene and propylene. In the moving catalyst dehydrogenation process, the catalyst is continuously circulated between a reactor and a regenerator.

A route for the production of propylene can be obtained by the dehydrogenation of propane through a catalytic dehydrogenation reaction. The dehydrogenation catalyst generally includes a noble metal catalyst on an acidic support, such as an alumina, silica alumina, or zeolite support. However, the dehydrogenation reaction is a strong endothermic reaction and requires a high temperature for the reaction to proceed at a satisfactory rate. Furthermore, the dehydrogenation reaction needs to be controlled to limit the degradation of the propane to form methane and ethylene, and the ethylene can be hydrogenated by the hydrogen released through the dehydrogenation of propane. In addition, the dehydrogenation process deactivates the catalyst by coking the catalyst. Accordingly, the catalyst needs to be regenerated on a regular basis after a relatively short time of operation or residence in the dehydrogenation reactor.

In connection with this, FIG. 1 shows a conventional process of separating and recovering propylene from a propane dehydrogenation product by a low-temperature separation process and through a C3 product splitter. The known process shown in FIG. 1 is a process of dehydrogenating propane to propylene, in which a propane-containing feed gas stream is preheated to 600 to 700° C. and dehydrogenated in a moving-bed dehydrogenation reactor, thereby obtaining a product gas stream containing propane, propylene and hydrogen as main components.

Meanwhile, the moving-bed reactor is advantageous in that a catalyst can be moved and thus a continuous catalyst regeneration system can be constructed. As one example of this moving-bed reactor, U.S. Pat. No. 6,472,577 discloses a continuous catalyst regeneration system including a catalyst bed. However, such a conventional fluidized bed dehydrogenation reactor has limitations in that the residence time of the catalyst is short and the conversion rate is low. Since the conversion rate for the dehydrogenation reaction is closely related to the basic unit and economic efficiency of the process, it is urgently required to develop a dehydrogenation reactor capable of improving the conversion rate in order to increase the efficiency of the continuous catalytic reaction-regeneration system.

DISCLOSURE

Technical Problem

The present invention has been conceived to meet the above-described technical requirement, and an object of the present invention is to provide a method for dehydrogenating an alkane, which may increase the total amount of heat supply by supplying reaction heat separately to each of reactor stages, and may adjust the molar ratio of hydrogen to propane in a feed gas stream to 0.4 or less, thereby reducing the hydrogen partial pressure and thus reducing the basic unit of the process and increasing yield and production.

Technical Solution

One aspect of the present invention for achieving the above-described object is directed to a method for dehydrogenating an alkane, the method including: a step of feeding into dehydrogenation reactors a feed gas stream containing a hydrocarbon to be dehydrogenated, hydrogen, and steam and performing dehydrogenation, wherein the dehydrogenation step is repeated in five or more sets, the dehydrogenation reactors have two parallel-connected reaction material heaters configured to heat the feed gas stream which is fed into each of the dehydrogenation reactors, and the steam is fed separately to the individual reactors for five or more sets of dehydrogenation steps; and a step of cooling and compressing a production gas stream resulting from the previous step, quenching the compressed product gas stream by passage through a cooling box, separating and purifying the product gas stream having passed through the cooling box, and recovering a product.

Advantageous Effects

According to the method of the present invention, an increase in propylene production and improvement in the basic unit of the process may be achieved by feeding steam into dehydrogenation reactors. In addition, improvement in the basic unit of the process and an increase in the total amount of heat supply may be achieved by supplying heat separately to each of five reactor stages, thereby increasing propylene production.

In addition, according to the present invention, an ethylene/propylene freezer is included in a cooling box, and thus it is possible to adjust the molar ratio of hydrogen to propane in the feed fed into the reactor to 0.4 or less, thereby reducing the hydrogen partial pressure and thus increasing the theoretical yield of the propane dehydrogenation reaction and increasing propylene production.

BEST MODE

Figure 1:
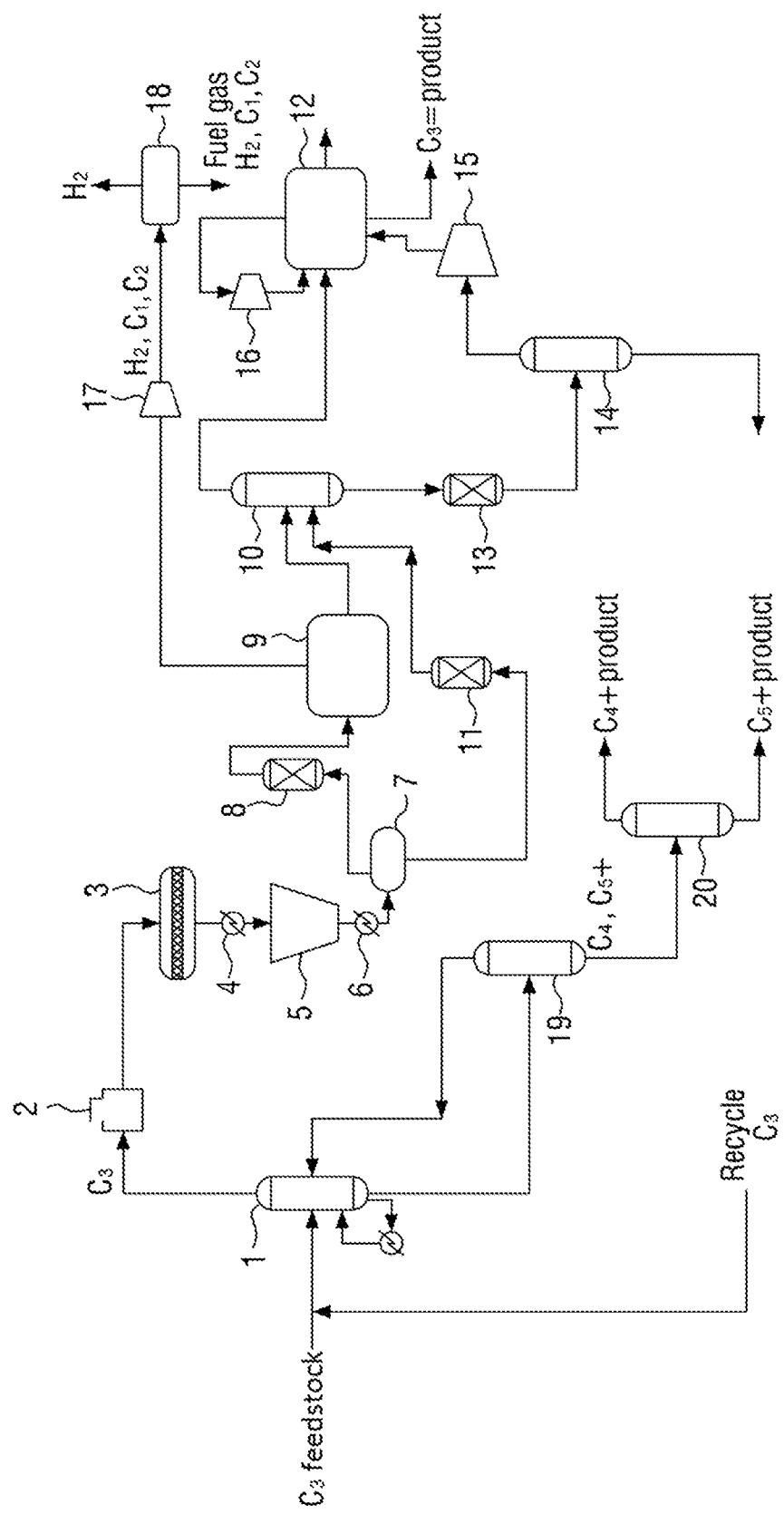
FIG. 1 is a process flow diagram showing a process of producing propylene by propane dehydrogenation according to a conventional art.

The present invention will be described in greater detail below with reference to the accompanying drawings.

Although common terms which are widely used currently have been selected as terms used in the present invention as much as possible, a term randomly selected by the applicant is used in a particular case. In this case, the meaning of a term should be understood by considering the meaning described or used in the detailed description of the invention, rather than simply considering the name of the term. Like reference numerals refer to like elements throughout the specification.

Although the accompanying drawings describe a particular shape of the dehydrogenation reactor of the present invention, this dehydrogenation reactor may have various shapes suitable for particular environments which are performed in particular applications. The broad application of the present invention is not limited to the specific embodiments which will be described below. Furthermore, the numerals in the drawings are used to represent a simple schematic diagram of the multi-stage dehydrogenation reactor of the present invention, and only the major components are shown in the drawings. Heat exchangers, internal heaters, moving pipes for catalyst transfer, pumps, and other similar components are omitted in the drawings. Using these components to modify the described dehydrogenation reactor is known to those skilled in the art, and does not depart from the scope and spirit of the appended claims.

It should be understood that various ranges and/or numerical limitations include iterative ranges of like magnitude falling within the expressly stated ranges or limitations.

The term "dehydrogenated hydrocarbon" as used herein is intended to include hydrocarbons whose molecules include at least two fewer hydrogen atoms than the molecules of a hydrocarbon to be dehydrogenated. Otherwise, the term hydrocarbon is intended to include substances whose molecules are composed only of the elements carbon and hydrogen. Accordingly, dehydrogenated hydrocarbons particularly include acyclic and cyclic aliphatic hydrocarbons having one or more C—C double bonds in the molecule.

Examples of such aliphatic dehydrogenated hydrocarbons are propene, isobutene, ethylene, 1-butene, 2-butene and propylene. In other words, the dehydrogenated hydrocarbons include, in particular, the monounsaturated linear hydrocarbons (n-alkenes) or branched aliphatic hydrocarbons (e.g., isoalkenes), and also the cycloalkenes. Furthermore, the dehydrogenated hydrocarbons are also intended to include the alkapolyenes (e.g., dienes and trienes) which include two or more carbon-carbon double bonds in the molecule. In addition, dehydrogenated hydrocarbons are also intended to include hydrocarbon compounds which are obtainable by starting from alkylaromatics, such as ethylbenzene or isopropylbenzene, through the dehydrogenation of the alkyl substituent. These are, for example, compounds such as styrene or α-methylstyrene.

The term "conversion rate" as used herein means the ratio of dehydrogenated hydrocarbon to fed hydrocarbon, which is converted in the single pass of the reaction gas through the dehydrogenation reactor.

The term "selectivity" means the moles of propylene which are obtained per mole of propane converted, and is expressed as the molar percentage.

The term "de-ethanizer" as used herein refers to a unit which separates a C1-C2 gas stream, containing methane, ethane, ethylene or the like, as a top stream, separates a C3-C4 gas stream, containing propane and propylene, as a bottom stream, and sends the C3-C4 gas stream to a "propane/propylene splitter." The C1-C2 gas stream is used as a cooling agent for a gas cooler or a fuel gas raw material in the process.

The "propane/propylene splitter" means a column which is designed to separate propylene from a mixture containing hydrocarbons having three or more carbon atoms. The "propane/propylene splitter" separates propylene as a top stream, separates a C3-C4 gas stream, containing propane, as a bottom stream, and sends the C3-C4 gas stream to a "depropanizer."

The "depropanizer" means a column which is designed to separate a hydrocarbon having four or more carbon atoms from a mixture containing hydrocarbons having three or more carbon atoms.

The term "C4+ hydrocarbon" as used herein mainly refers to a hydrocarbon having four or more carbon atoms. The term "C5+ hydrocarbon" as used herein mainly refers to a hydrocarbon having five or more carbon atoms.

Figure 2:
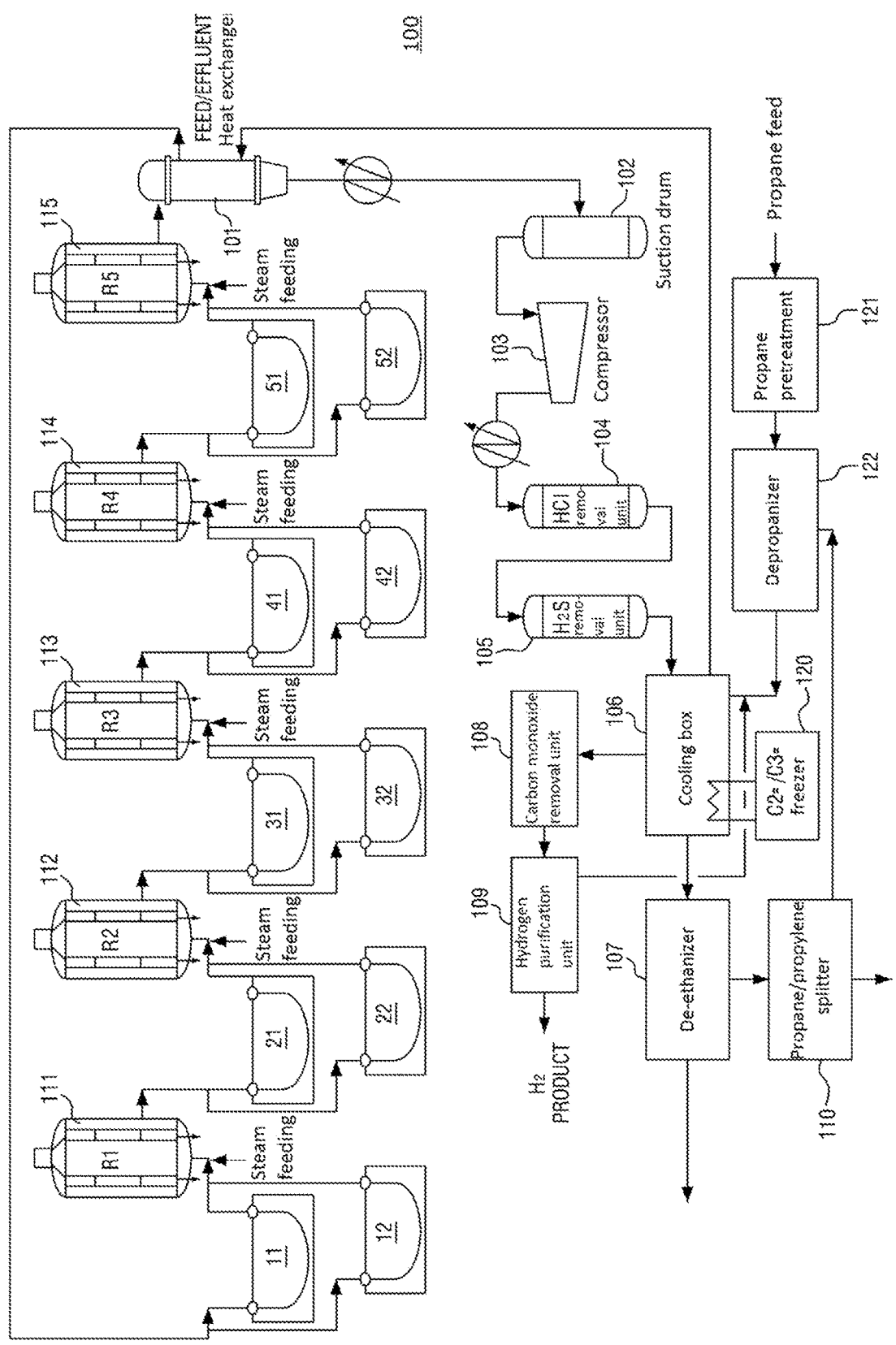
FIG. 2 is a process flow diagram schematically showing a process of dehydrogenating an alkane hydrocarbon according to an embodiment of the present invention.

FIG. 2 is a process flow diagram showing a method and an apparatus for dehydrogenating an alkane according to one embodiment of the present invention.

Referring to FIG. 2, in the method of the present invention, an alkane is dehydrogenated through: a step of feeding into dehydrogenation reactors a feed gas stream containing an alkane hydrocarbon to be dehydrogenated, hydrogen, and steam and performing dehydrogenation, wherein the dehydrogenation step is repeated in five or more sets, the dehydrogenation reactors have two parallel-connected reaction material heaters configured to heat the feed gas stream which is fed into each of the dehydrogenation reactors, and the steam is fed separately to the individual reactors for five or more sets of dehydrogenation steps; and a step of cooling and compressing a production gas stream from the previous step, quenching the compressed product gas stream by passage through a cooling box, separating and purifying the product gas stream having passed through the cooling box, and recovering a product.

A feed gas stream, such as propane, is fed into at least five dehydrogenation reactors 111 to 115 and subjected to catalytic dehydrogenation. In this process step, propylene is produced by partially dehydrogenating the propane over a dehydrogenation-active catalyst in the dehydrogenation reactors. Additionally, hydrogen and small amounts of methane, ethane, ethene and C4+ hydrocarbons (n-butane, isobutane, butene) are produced.

In the present invention, the dehydrogenation reaction is sequentially performed in at least five sets. Specifically, propane is dehydrogenated to propylene in one set, and the gas stream subjected to the first dehydrogenation reaction is introduced sequentially into the second, third, fourth and fifth dehydrogenation reactors 112, 113, 114 and 115 sequentially connected to the first reactor 111, and is subjected again to the dehydrogenation reaction. That is, in the multi-stage dehydrogenation, a reaction product is introduced into one set and subjected to dehydrogenation, after which the reaction product is introduced into subsequent stages and dehydrogenation is repeatedly performed in proportion to the number of stages of subsequent reactors.

In the present invention, the feed gas stream is subjected to at least five sets of dehydrogenation reactions by at least five dehydrogenation reactors 111, 112, 113, 114 and 115. However, propane is fed to the first 111 to fifth reactor 115 as a feed gas stream, hydrogen is fed to the front end of the first reactor 111, and steam is additionally fed to the first reactor 111 to fifth reactor 115. By doing so, it is possible to improve propylene production and reaction selectivity, and reduce the basic unit of the process.

In principle, alkane dehydrogenation may be performed in any type of reactor known in the art. For example, the dehydrogenation reactors 111, 112, 113, 114 and 115 may be tubular reactors, stirred-tank reactors, or fluidized-bed reactors. As another example, the reactors may be fixed-bed reactors, tubular fixed-bed reactors, or plate-type reactors.

Referring to FIG. 2, a dehydrogenation reaction apparatus 100 which is used in the practice of the present invention includes a first reactor 111, a second reactor 112, a third reactor 113, a fourth reactor 114, and a fifth reactor 115. A reactant stream which is a hydrocarbon gas feed is indicated by the solid arrow. The first reactor 111 is fed with either the feed gas stream containing a hydrocarbon (e.g., propane) to be dehydrogenated, hydrogen, or steam, and the first reactor 111 is also fed with a heated gas stream supplied from two parallel-connected reaction material heaters 11 and 12. The reactant stream is fed directly into the second reactor 112 and subjected to dehydrogenation in the second reactor, and a first product stream is recovered from the second reactor. Then, the first product stream and the catalyst used for the reaction in the first reactor 111 are fed into the second reactor 112 having two parallel-connected reaction material heaters 21 and 22 and subjected to dehydrogenation in the second reactor 112, and a second product stream is recovered from the second reactor 112.

Then, the second product stream, stream, and the catalyst stream used for the reaction in the second reactor 112 are fed into the third reactor 113 having two parallel-connected reaction material heaters 31 and 32 and subjected to dehydrogenation in the third reactor 113, and a third product stream is recovered from the third reactor 113. The third product stream and the catalyst stream used for the reaction in the third reactor 113 are fed into the fourth reactor 114 having two parallel-connected reaction material heaters 41 and 42 and subjected to dehydrogenation in the fourth reactor 114. The fourth product stream, steam, and the catalyst stream used for the reaction in the fourth reactor 114 are fed into the fifth reactor 115 having two parallel-connected reaction material heaters 51 and 52 and subjected to dehydrogenation in the fifth reactor 115, and a fifth product stream is recovered from the fifth reactor 115 into a product splitter 101. The "product stream" generated in each reactor stage means a reaction product produced by the dehydrogenation reaction. Specifically, it means a gas, a liquid, or a gas or liquid containing a dispersed solid, or a mixture thereof, which may contain hydrogen, propane, propylene, ethane, ethylene, methane, butane, butylene, butadiene, nitrogen, oxygen, vapor, carbon monoxide, carbon dioxide or the like.

The dehydrogenation reaction is repeated in at least five sets as described above, and thus the reaction heat supplied to each stage may decrease and the load of the reaction material heaters may decrease, thereby increasing reaction selectivity and thus resulting in a decrease in the basic unit of the process. In addition, since all the dehydrogenation reactors are adiabatic reactors, it is possible to perform an additional reaction by the amount of heat supplied from the reaction material heaters disposed in front of one additional reactor stage, thereby reducing propylene production.

In the present invention, since two parallel-connected reaction materials configured to supply reaction heat are disposed in front of each reactor stage, the load of the reaction material heaters is reduced by half, the temperature uniformity is maintained and the operating temperature is down-regulated, thereby improving the basic unit of the process.

In the present invention, steam is fed separately into the individual reactors 111, 112, 113, 114 and 115 in order to prevent coking of the catalyst. In the method of the present invention, steam is introduced during the dehydrogenation reaction, and thus coke formed on the catalyst is removed by decomposing it into hydrocarbons, carbon monoxide and hydrogen. In particular, in the present invention, steam is fed into each of the five dehydrogenation reactors. When coke is removed by steam as described above, it is possible to prevent the performance of catalyst active sites from being reduced due to coke formation, thereby improving the long-term performance of the catalyst. In addition, propane can selectively bind to active sites formed on the catalyst surface by by-products, such as ethane, ethylene and methane, thereby increasing the production rate of the main reaction in which propane is dehydrogenated to propylene and hydrogen and thus increasing propylene production and reaction selectivity.

After the completion of the dehydrogenation reaction, the product gas stream produced in the fifth reactor 115 which is the last reactor stage is cooled, compressed, and quenched by passage through a cooling box 106, and the product gas stream which has passed through the cooling box is separated, purified and recovered. During quenching in the cooling box 106, the hydrogen/alkane hydrocarbon in front of the "first reactor 111" may be down-regulated to 0.4 or less using an ethylene/propylene freezer 120.

The reaction product is heat-exchanged through a heat exchanger 101, and then transferred into a suction drum 102 and separated by boiling point, and a "C5+ hydrocarbon" is separated as a bottom stream. The top stream (gas-phase product) from the suction drum 102 is subjected to a pressurization and cooling process in a compressor 103, and then passes sequentially through a hydrogen chloride removal unit 104 and a hydrogen sulfide removal unit 105. Then, it is additionally subjected to a cooling and compression process through a cooling box 106 which is a freezing system, and at the same time, hydrogen containing carbon monoxide is sent to a "carbon monoxide removal unit 108", and a hydrocarbon gas stream containing propane and propylene is transferred into a de-ethanizer 107. Downstream of the compressor 103 are disposed a hydrogen chloride removal unit 104 configured to remove hydrogen chloride (HCl) generated in the dehydrogenation reaction and catalyst regeneration process, and a hydrogen sulfide removal unit 105 configured to a sulfide contaminant discharged from the compressor. This hydrogen chloride removal unit 104 and this hydrogen sulfide removal unit 105 may remove contaminants by an adsorbing agent or an adsorbent.

The product obtained from the reactor after the dehydrogenation reaction contains a C4 mixture containing propylene, as well as carbon monoxide, unreacted propane, nitrogen, oxygen, steam, and carbon dioxide. In particular, in the method of the present invention, steam is introduced into the feed gas stream in order remove coke, and hence coke formed on the catalyst in the reactor reacts with steam ($H_2O$) to produce carbon monoxide and hydrogen ($H_2$). These by-products should be separated and discharged out of the system so as not to be continuously accumulated in the process. Thus, in the present invention, a carbon monoxide removal unit 108 configured to remove carbon monoxide is disposed next to the cooling box 106, and a gas stream from which the carbon monoxide has been removed is sent to a hydrogen purification unit 109.

The carbon monoxide removal unit 108 may include hopcalite, which is a mixed oxide of copper-manganese which is highly active for the reaction between carbon monoxide and oxygen. In the presence of hopcalite, highly toxic hydrogen monoxide reacts with oxygen to form carbon monoxide. In addition, carbon monoxide may be removed by adsorption with an adsorbent composition including a copper oxide, a zinc oxide and an aluminum oxide.

The product gas stream obtained from the dehydrogenation reactor may further be subjected to a post-treatment process in order to obtain a highly pure product. The post-treatment process includes a quenching step using a quenching tower, a compression step using a compressor, a dehydration step using a dehydration device, and a separation step using a cooling box 106. In the present invention, the reaction product obtained from the dehydrogenation reactor is passed through the cooling box, and, thus, when the reaction product is the product of propane dehydrogenation, it is separated into a hydrocarbon mixture, which contains C1, C2, C3 and C4, and hydrogen.

The ethylene/propylene freezer 120 which may be used in the cooling box 106 may use a propylene-based or ethylene-based solvent as a refrigerant, or, if necessary, may perform the same function using another refrigerant. For example, the refrigerant may be one or a mixture of two or more selected from the group consisting of methane, ethylene and propylene. It is to be understood that the propylene-based solvent means propylene or a compound containing propylene, and the ethylene-based solvent means ethylene or a compound containing ethylene.

The molar ratio of hydrogen to hydrocarbon (propane) in the feed gas stream which is used in the dehydrogenation process according to the present invention may be down-regulated to 0.4 or less. In the present invention, in order to perform the reaction process such that the molar ratio of hydrogen to propane in the feed gas stream can be down-regulated to a range of 0.4 or less to 0, the ethylene/propylene freezer 120 is used in the cooling box 106 to meet an energy balance corresponding to the reduction in the hydrogen proportion. Due to this feature, the ratio of hydrogen to propane can be down-regulated, and thus the reaction yield can be increased by about 5% to 10% compared to a conventional process and the reaction selectivity can also be increased by 2 to 5%.

Prior to the de-ethanizer 107 process, components, such as hydrogen and carbon monoxide, which have the lowest boiling point among the overall process, are separated from the cooling box 106, pressurized, and then recovered as hydrogen from a hydrogen purification unit 108. Meanwhile, a propylene-containing gas stream which has passed through the cooling box 106 and the de-ethanizer 107 is separated into propane and a C4 mixture in a propane/propylene splitter 108, and the propylene is purified and recovered.

In a propane pretreatment process 121, impurities, such as water, metal impurities, and carbon monoxide, are removed from the propane feed gas stream, and a propane gas stream containing a very small amount of a C4 mixture is transferred into a depropanizer 122.

In the depropanizer 122, at least a portion of C4+ hydrocarbons is separated as a bottom stream and high-purity propane is transferred to the cooling box 106, while a purified propylene-containing product containing C3 or lighter hydrocarbons and hydrogen is separated as a top stream. In the depropanizer 122, butane, butylene, butadiene, and the like, which cause coke formation, are removed before the feed gas stream is fed into the first dehydrogenation reactor 111, and high-purity propane is transferred to the cooling box 106.

The high-purity propane stream supplied to the depropanizer 122 is mixed with the high-purity hydrogen supplied from the hydrogen purification unit 109, and then it is heated by low-temperature heat exchange in the cooling box 106, and transferred to and further heat-exchanged in the heat exchanger 101. Then, it is further heated by the reaction material heaters 11 and 12 and is fed again into the first reactor 111. In the depropanizer 122, a C4 gas stream containing butane is separated as a bottom stream and recycled as a raw material for a process fuel gas.

In the cooling box 106, the high-temperature hydrocarbon stream supplied from the $H_2S$ removal unit 105 is subjected to a cooling and compression process and separated into carbon monoxide-containing hydrogen and a hydrocarbon stream, which are then transferred to the carbon dioxide removal unit 108 and the de-ethanizer 107, respectively.

While the present invention has been described in connection with the preferred embodiments of the present invention, the scope of the present invention is not limited to the above-described embodiments, and it will be apparent that many modifications may be made by those skilled in the art without departing from the technical spirit of the present invention. Therefore, the true scope of the present invention should be defined based on the appended claims and equivalents thereof. For example, although the propane dehydrogenation reaction for producing propylene has been mainly described in detail above, this disclosure may be applied to a dehydrogenation reaction that converts an alkane containing two or more carbon atoms, for example, ethane, n-butane, isobutane, normal butane, pentane, hexane, or octane, into the corresponding octane, as understood by those skilled in the art through this disclosure.

The invention claimed is:

1. A method for dehydrogenating an alkane, the method comprising:
    feeding into serially-connected dehydrogenation reactors a feed gas stream containing an alkane hydrocarbon to be dehydrogenated, hydrogen, and steam,
        wherein a ratio of hydrogen to alkane hydrocarbon in the feed gas stream is 0.4 or less;
    dehydrogenating the alkane hydrocarbon,
        wherein the dehydrogenating is conducted in each of the serially-connected dehydrogenation reactors and is repeated in five or more sets,
        each of the serially-connected dehydrogenation reactors has two parallel-connected reaction material heaters disposed in front of the dehydrogenation reactor and configured to heat the feed gas stream, which is alkane hydrocarbon and hydrogen fed into the dehydrogenation reactor, and
        the steam is fed separately from the feed gas stream into each of the serially-connected dehydrogenation reactors;
    cooling and compressing a product gas stream obtained from the last dehydrogenation reactor of the serially-connected dehydrogenation reactors to generate a compressed product gas stream;
    quenching the compressed product gas stream by passing through a cooling box comprising an ethylene/propylene freezer;
    separating a gas stream from the cooling box and removing carbon monoxide (CO) from the gas stream thereby obtaining a carbon monoxide-depleted gas stream;
    transferring the carbon monoxide-depleted gas stream to a hydrogen purification stage;
    maintaining the ratio of hydrogen to alkane hydrocarbon in the feed gas stream to 0.4 or lower by passing the feed gas stream through the cooling box through a passage different from the product gas stream while quenching of the compressed product gas stream is being conducted,
        wherein the feed gas stream is then supplied to a front inlet of the first reactor;

separating and purifying a compressed and cooled product gas stream having passed through the cooling box; and recovering a product comprising a dehydrogenated hydrocarbon.

2. The method of claim 1, wherein the ethylene/propylene freezer uses a propylene-based or ethylene-based solvent as a refrigerant.

3. The method of claim 1, further comprising:

removing hydrogen chloride (HCl) from the compressed product gas stream; and removing hydrogen sulfide ($H_2S$) from the compressed product gas stream.

4. The method of claim 1, further comprising:

pretreating a propane feed;

transferring the pretreated propane feed to a depropanizer;

separating at least a portion of a C4+ hydrocarbon as a bottom stream from the depropanizer;

transferring propane separated by the depropanizer to the cooling box; and separating a purified propylene-containing product, which contains a C3 or lighter hydrocarbon and hydrogen, as a top stream from the depropanizer.

5. The method of claim 1, wherein the alkane hydrocarbon to be dehydrogenated contains one of ethane, propane, isobutane, n-butane, pentane, hexane, heptane and octane.

6. The method of claim 2, wherein the alkane hydrocarbon to be dehydrogenated contains one of ethane, propane, isobutane, n-butane, pentane, hexane, heptane and octane.

7. The method of claim 3, wherein the alkane hydrocarbon to be dehydrogenated contains one of ethane, propane, isobutane, n-butane, pentane, hexane, heptane and octane.

8. The method of claim 4, wherein the alkane hydrocarbon to be dehydrogenated contains one of ethane, propane, isobutane, n-butane, pentane, hexane, heptane and octane.

* * * * *